US006632664B1

(12) United States Patent
Saitoh et al.

(10) Patent No.: US 6,632,664 B1
(45) Date of Patent: Oct. 14, 2003

(54) AVIAN INFECTIOUS HERPESVIRUS RECOMBINANTS AND RECOMBINANT VACCINES PREPARED WITH THE USE OF THE SAME

(75) Inventors: Shuji Saitoh, Kawasaki (JP); Takashi Okuda, Kawasaki (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/509,871

(22) PCT Filed: Oct. 2, 1998

(86) PCT No.: PCT/JP98/04468

§ 371 (c)(1),
(2), (4) Date: Jul. 5, 2000

(87) PCT Pub. No.: WO99/18215

PCT Pub. Date: Apr. 15, 1999

(30) Foreign Application Priority Data

Oct. 3, 1997 (JP) .............................................. 9-271445

(51) Int. Cl.[7] ...................... A61K 39/12; A61K 39/245; A61K 39/255; C12N 15/36; C12N 15/869
(52) U.S. Cl. ................................. 435/320.1; 435/320.1; 435/235.1; 424/199.1; 424/204.1; 424/201.1; 424/202.1; 424/229.1; 424/810
(58) Field of Search ............................ 424/199.1, 201.1, 424/202.1, 229.1, 204.1, 810; 435/235.1, 320.1

(56) References Cited

U.S. PATENT DOCUMENTS 5,470,734 A * 11/1995 Sondermeirjer et al. . 424/229.1
5,733,554 A * 3/1998 Audonnet et al. ........ 424/199.1
5,853,733 A * 12/1998 Cochran et al. ......... 424/199.1
5,980,906 A * 11/1999 Audonnet et al. ........ 424/199.1

FOREIGN PATENT DOCUMENTS

| JP | 8-337539 | 12/1996 |
|---|---|---|
| JP | 9-20682 | 1/1997 |
| WO | 95/29248 | 11/1995 |
| WO | 96/05291 | 2/1996 |
| WO | 96/21034 | 7/1996 |
| WO | WO 97/49826 | 12/1997 |
| WO | WO 98/27215 | 6/1998 |
| WO | WO 98/33928 | 8/1998 |

OTHER PUBLICATIONS

Morgan et al. Avian Diseases 1992, vol. 36, pp. 858–870.*
Glorioso et al. Advances Pharmacology, 1997, vol. 40, pp. 103–136.*
Raphael Dareil, Michel Bublot, Eliane Laplace, Jean–Francois Bouquet, Jean–Christophe Audonnet, Michel Riviere, "Herpesvirus of Turkey Recombinant Viruses Expressing Infectious Bursal Disease Virus (IBDV) VP2 Immunogen Induce Protection against an IBDV Virulent Challenge in Chickens", Virology, 1995, vol. 211, No. 2, p. 481–490.

* cited by examiner

*Primary Examiner*—James Housel
*Assistant Examiner*—Bao Qun Li
(74) *Attorney, Agent, or Firm*—Armstrong, Westerman & Hattori, LLP

(57) ABSTRACT

An avian infectious recombinant herpesvirus is prepared by inserting a foreign gene, in particular a heterologous antigen gene, into an insertion site in an untranslated genetic region in the genome. A chicken vaccine comprising such a recombinant virus is also provided.

25 Claims, No Drawings

SEQUENCE LISTING

<160> NUMBER OF SEQ ID NOS: 23

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide for primer

<400> SEQUENCE: 1

```
ccccgaattc atggaagaaa tttcc                                          25
```

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide for primer

<400> SEQUENCE: 2

```
cgcgggcctt attggccaaa acacacctct aacggttact                          40
```

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide for primer

<400> SEQUENCE: 3

```
gcgcggccaa taaggccaaa acacagtaac cgttagaggt                          40
```

<210> SEQ ID NO 4
<211> LENGTH: 28
<212> TYPE: DNA
<213> ORGANISM: Artificial Sequence
<220> FEATURE:
<223> OTHER INFORMATION: Synthetic oligonucleotide for primer

<400> SEQUENCE: 4

```
ccccaagctt tcaagtgata ctgcgtga                                       28
```

<210> SEQ ID NO 5
<211> LENGTH: 37
<212> TYPE: DNA
<213> ORGANISM: Artificial Sequence
<220> FEATURE:
<223> OTHER INFORMATION: Synthetic oligonucleotide for primer

<400> SEQUENCE: 5

```
gcgcggccaa taaggccaac atcgggacgt acatcat                             37
```

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide for primer

<400> SEQUENCE: 6

```
gcgcggcctt attggcctta aataccgcgt ttggagtaaa                          40
```

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide for primer

<400> SEQUENCE: 7

```
agctgccccc ccggcaagct tgca                                           24
```

<210> SEQ ID NO 8
<211> LENGTH: 17
<212> TYPE: DNA

```
<213> ORGANISM: Artificial Sequence
<220> FEATURE:
<223> OTHER INFORMATION: Synthetic oligonucleotide for primer

<400> SEQUENCE: 8
tcgacatttt tatgtac                                                    17

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide for primer

<400> SEQUENCE: 9
aattcggccg gggggccag ct                                               22

<210> SEQ ID NO 10
<211> LENGTH: 14
<212> TYPE: DNA
<213> ORGANISM: Artificial Sequence
<220> FEATURE:
<223> OTHER INFORMATION: Synthetic oligonucleotide for primer

<400> SEQUENCE: 10
ggcccccccg gccg                                                       14

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide for primer

<400> SEQUENCE: 11
agcttgccaa taaggctgca                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide for primer

<400> SEQUENCE: 12
atggcccgcc ggctgaccgc                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide for primer

<400> SEQUENCE: 13
gcggtcagcc ggcgggccat                                                 20

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide for primer

<400> SEQUENCE: 14
ggtaaactgc agacttggca gt                                              22
```

```
<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide for primer

<400> SEQUENCE: 15
actgccaagt ctgcagttta cc                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide for primer

<400> SEQUENCE: 16
atggcccgcc atgcattatg cc                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide for primer

<400> SEQUENCE: 17
ggcataatgc atggcgggcc at                                              22

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide for primer

<400> SEQUENCE: 18
cgggagctct aattgtttgt g                                               21

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide for primer

<400> SEQUENCE: 19
cgggaattcg cttacaattt                                                 20

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide for primer

<400> SEQUENCE: 20
cgggggccct aattgtttgt g                                               21

<210> SEQ ID NO 21
<211> LENGTH: 20
<212> TYPE: DNA
<213> ORGANISM: Artificial Sequence
<220> FEATURE:
```

```
<223> OTHER INFORMATION: Synthetic oligonucleotide for primer

<400> SEQUENCE: 21
cggggtaccg cttacaattt                                              20

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide for primer

<400> SEQUENCE: 22
gcaagcttgc gatgacgaac ctgc                                         24

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide for primer

<400> SEQUENCE: 23
gcgtcgactc acctccttag ggccc                                        25
```

AVIAN INFECTIOUS HERPESVIRUS RECOMBINANTS AND RECOMBINANT VACCINES PREPARED WITH THE USE OF THE SAME

FIELD OF THE INVENTION

The present invention relates to a recombinant herpesvirus of turkeys (hereinafter referred to as BVT) and a recombinant Marek's disease virus (hereinafter referred to as MDV), in which an foreign gene has been integrated into a non-essential region of the genome of HVT or MDV, and vaccines employing said recombinant.

BACKGROUND ART

Conventionally known virus vector vaccines that are prepared using gene recombinant technology include vaccines that employ a virus of the genus poxvirus as a vector (Ogawa R. et al., Vaccine, 8:486–490 (1990)), vaccines that employ adenovirus as a vector (HSU, K. H. et al., Vaccine, 12;607–612 (1994)), vaccines that employ baculovirus as a vector, as well as vaccines that employ a virus of the genus herpesvirus as a vector (Shin, M. -F. et al., Proc. Natl. Acad. Sci. U.S.A., 81:5867–5870 (1984)). Among them, recombinant vector vaccines based on the genus herpesvirus are under intensive study in recent years.

As virus vectors that permit the expression of a gene for a foreign antigen, there are known human herpesvirus (HSV), Aujeszky's disease virus (pseudorabies virus; PRV) (Van Zijl M. et al., J. Virol., 65:2761–2765 (1991)), herpesvirus of turkey (HVT) (Morgan R. W. et al., Avian Dis. 36:858–870 (1992)), Marek's disease virus (MDV), and the like. Since, HVT virus and vaccine strain MDV, among them, have high safety in poultry that are the subject of vaccination and have good vaccine characteristics, they are attracting attention as vector viruses for avians.

Unlike poxvirus that has a mode of infection in which the virus is once released into the blood from the infected cell and then it infects another call during its infection from the infected cell to another cell, HVT and MDV establish infection via a cell-cell interaction to an adjacent cell. Thus, they are relatively free from the influences of HVT- or MDV-specific antibodies present in the circulating blood.

Conventionally, problems have been recognized in that the efficacy of live virus vaccines is attenuated by the presence of maternal antibody from the mother bird, resulting in the failure of exhibiting their full effects.

In recent years, methods of inoculating vaccines into developing chicken eggs have been developed as one of the methods of vaccination to chickens, and the usefulness of HVT or MDV as a vaccine is gaining recognition.

However, conventionally known genetic regions so far reported for construction of recombinant BVT or MDV for foreign antigen were only genetic regions that are considered non-essential for survival of HVT such as the TK region (Ross L. et al., 16th International Herpes virus Workshop (1991)), the US10region (Sakaguchi M. et al., Vaccine, 12:953–957 (1994)), and the US2 region (Sondermeijer, P. J. et al., Vaccine, 11:349–358 (1993)). Such integration into non-essential regions can attenuate the antigenicity of HVT or MDV since it causes the expression of a foreign gene in stead of a gene that, though non-essential, should naturally be expressed in HVT i.e. a gene that will make an antigenic determinant. In addition, the possibility cannot be ruled out that the genetic machineries (enhancers, promoters, terminators, etc.) involved in the transcription or translation of the open reading frame for the inserted region may adversely affect the expression of the inserted gene.

In fact, there are reports that the deletion of genetic regions encoding proteins that are considered to be non-essential or the integration therein of foreign genes resulted in the modification of viral morphology or the reduction in antigenicity. Furthermore, the integration of foreign genes has been used, in some cases, as a method of preparing attenuated vaccines.

Another report demonstrates that the insertion of a foreign gene into the TK region and the expression thereof resulted in the decreased antigenicity of the expressed gene (Ross L. et al., J. Gen. Virol., 74:371–377 (1993)). This method also has a number of problems as a vaccine in that many antigen genes cannot be inserted since the length of antigen genes that can be inserted into specific ORFs is limited.

As a result of intensive study to solve the above problems, the inventors of the present invention have found that there are the gene insertion regions of HVT or MDV into which a variety of genes for foreign antigen can be inserted and the antigen protein can be stably expressed, i.e. the untranslated region of HVT or MDV mentioned above, that genes of various foreign antigens can be inserted therein, and that by preparing recombinant HVT or MDV into which these genes of foreign antigen have been inserted and then infecting these recombinant viruses to the hosts, adequate vaccination effect cat be conferred to the host, and thereby have completed the present invention.

DISCLOSURE OF THE INVENTION

As a result of intensive study to solve the above problems, the inventors of the present invention have prepared a recombinant virus in which a foreign gene has been inserted into a specific site in a untranslated region of a virus DNA belonging to the avian infectious herpesvirus and found that said recombinant virus can be used as a vaccine, and thereby have completed the present invention.

Thus, the present invention relates to avian infectious recombinant herpesviruses in which a foreign gene has been inserted into a genetic region that is an untranslated region in the genome. Preferably, the virus mentioned above is herpesvirus of turkeys (HVT) and Marek's disease virus (MDV).

The above untranslated region is preferably an untranslated region present in the open reading frame of herpesvirus of turkeys or the open reading frame of Marek's disease virus, each corresponding to the open reading frame of human herpes simplex virus. A specifically preferred insertion site for a foreign gene is at least one insertion site selected from the group consisting of sites in (1) between UL44 and UL45, (2) between UL45 and UL46, (3) between UL41 and UL42, (4) between UL40 and UL41, (5) a region located downstream of the gB gene, (6) between UL53 and UL54, and (7) between UL36 and UL37.

The above foreign gene is preferably a gene derived from a pathogen of avian infectious diseases, and most preferably an antigen gene derived from a pathogen selected from the group consisting of viruses, bacteria, fungi, and protozoa. Furthermore, the above foreign gene is preferably a gene derived from a pathogen selected from the group consisting of Newcastle disease virus (NDV), Gumboro disease virus (infectious bursal disease virus: IBDV), infectious laryngotracheitis virus (ILTV), infectious bronchitis virus (IBV), mycoplasma (MG), and coccidia.

The present invention also relates to a chicken vaccine comprising the above recombinant virus as an active ingredient.

EBODIMENT FOR CARRYING OUT THE INVENTION

The present invention will now be explained hereinbelow in more details.

Viruses for Use in the Present Invention

Of the viruses that infect avians, viruses for use in the present invention are preferably those that belong to the genus herpesvirus (avian infectious herpesvirus), because viruses that belong to the genus herpesvirus have a property of permanently surviving in the body of an infected animal in the state of latent infection or persistent infection.

Of the avian infectious herpesviruses, specifically herpesvirus of turkey or Marek's disease virus (MDV) is preferred. Their effectiveness as a vaccine can be expected because the above viruses have a long infection period and are expected to confer to avians vaccination effects for a long period of time.

HVT or MDV

HVT or MDV for use in the present invention may include, but not limited to, naturally occurring ones or those available from ATCC etc. with or without charge.

Preferred examples of HVT include those that belong to the gamma herpesvirus subfamily, that are originally nonpathogenic, and that are noncarcinogenic and are used as a vaccine for poultry. Specifically, there can be mentioned FC126 (ATCC VR-584B), PB-THV1, H-2, YT-7, WTHV-1, EPRS-26, and the like. For example, the FC126 strain may be preferably used. Furthermore, specific examples of MDV include CV1988, SR1, and the like.

In order to construct a recombinant virus of the present invention, initially, the above virus is propagated in a suitable host cell and then the genomic DNA is obtained. Then the untranslated region of the genomic DNA is identified and then a foreign gene described below is inserted into the region.

The host and the conditions for propagating the virus are selected as appropriate depending on the virus to be propagated. For example, when HVT is to be propagated, CEF, a embryonated egg, a chicken kidney dell, and the like are used as the host cell. It may be cultured in a culture medium such as Eagle's MEM, Leibowitz-L-15/McCoy 5A (1:1 mixture) culture medium at about 37° C. for 3 to 4 days.

DNA is extracted from the virus infected cells cultured as above according to a conventional method. Thus, the cells grown in monolayers are scraped, and then spun to harvest the supernatant. After protein is denatured in the lysis buffer and removed, DNA is extracted with phenol and ethanol.

The untranslated region of the viral DNA thus obtained may be identified as described below.

Untranslated regions as used herein refer to a region of nucleotides that have no ORF and do not define an amino acid sequence of protein to be expressed by translation, and a region of nucleotides in which the ORF is not involved in any of transcription, translation, or protein expression. The nucleotide sequences contained in this region may be those that have substitutions, deletions, or additions of bases, unless they include an ORF.

Regions for Insertion of Foreign Gene

For the purposes of this invention, regions into which foreign genes are inserted are termed as insertion regions for foreign gene, and sites into which foreign genes are inserted are termed as sites for insertion of foreign gene.

Regions for insertion of foreign gene can be obtained as described below. By way of example, HVT or MDV will be explained.

The untranslated regions of these viruses may be obtained as described below. First, sequences flanking a sequence estimated to be an untranslated region are selected from regions that have been identified, such as human herpes simplex virus type I (HSV-I) of which entire nucleotide sequence has been determined and HVT and MDV-1 sequences that have a high homology therebetween.

Then, DNA primers are synthesized based on these sequences, and a polymerase chain reaction (PCR) is carried out under predetermined conditions using the DNA of HVT or MDV as a template to amplify a specific gene.

The absence of an ORF in the amplified gene is confirmed by DNA sequence analysis and the positions where the genetic machineries (enhancers, promoters, terminators, etc.) involved in the transcription or translation of the ORE are not present are also located, and then insertion regions for foreign gene are determined.

In order to clarify that the region is non-essential for viral propagation and that a foreign gene can be introduced into this region, the addition, deletion, or replacement of a specific sequence is carried out in the region, which is then infected to CEF (chick embryo fibroblast), and changes in infectivity and a propagating property beforehand after such modifications are investigated.

The above-mentioned addition, deletion, or replacement of a specific sequence can be carried out using standard tools such as in vitro mutagenesis, PCR, site-directed mutagenesis, and site-specified mutation as described in Japanese Examined Patent Publication (Kokoku) No. 6-16709.

CEF is infected at m.o.i≈1, grown at 37° C. for 3 to 4 days, and then viral propagation, cell morphology, plaque morphology, and cell immortality are observed.

As a result, if it is confirmed that there are no differences in cell and plaque morphology from the strain before nucleotide modification, and that the difference in viral propagation from the strain before nucleotide modification is within ±20% as a mean of five repeat runs, it is thereby concluded that said site is a region into which a foreign gene can be inserted (a possible insertion region for foreign gene). The size of the insertion region for foreign gene including the untranslated region and regions flanking it is sufficiently 10 bp or more, preferably 100 bp or more, and more preferably 500 bp or more.

Insertion sites for foreign gene are not limited as long as they are within the untranslated region. Specific examples include sites in (1) between UL44 and UL45 and between UL45 and UL46, (2) between UL41 and UL42, (3) between UL40 and UL41, (4) a region located downstream of the gB gene, (5) between UL53 and UL54, (6) between UL36 and UL37, and the like. They are described for HSV-1 in the Proceedings of the 16th Herpes Virus Workshop (held at Pacific Grove in California, U.S.A., on Jul. 7–12, 1991).

Among them, preferred sites include (1) and (4) for which homology has been confirmed in the ORF in not only HSV-1 but also MDV, and more preferably (1) for which an untranslated region in between ORFs can be estimated.

Construction of Plasmids Containing a Foreign Gene

In order to insert a foreign gene in an untranslated region of HVT or MDV, it is necessary to clone a sequence containing the untranslated region into a plasmid in advance, but the plasmid is not limited.

For example, there can be mentioned plasmids such as pBR322, pBR325, pBR327, pBR328, pUC18, pUC19, pUC7, pUC8, and pUC9, and phages such as lambda phage and M13 phage, and cosmids such as pHC79.

An untranslated region obtained as mentioned above is integrated into these plasmids according to a conventional method.

In order to insert a foreign gene into the untranslated region integrated as above, mutation is carried out at a specific site of the untranslated region that was cloned in a plasmid as above to make a new cleavage site for restriction enzymes, and then the foreign gene is inserted into the site.

A method of carrying out mutation may be a conventional method, and a method commonly used by a person skilled in the art such as in vitro mutagenesis and PCR can be used. Thus, in the PCR method, a mutation such as the deletion, replacement, or addition of 1 to 2 nucleotides in the PCR primer is carried out, and the primer is then used to create a mutation.

For the purposes of this invention, the foreign gene to be inserted herein preferably contains both of a self-derived gene that originally is not included in the region and a non-self-derived gene, and is preferably an antigen gene of an avian infectious herpesvirus.

Examples of such genes include genes derived from a pathogen of avian infectious diseases. Examples of pathogens that cause infection in avians include virus, bacteria, fungi, protozoa, and the like. Antigen genes contained in these pathogens i.e. genes encoding determinants of antigen can be preferably used.

Specific examples of such pathogens include New Castle disease virus (NDV) and Gumboro disease (infectious bursal disease virus) (IBDV) that are lifelong threats to chickens, infectious laryngotracheitis virus (ILTV), infectious bronchitis virus (IBV), mycoplasma (MG), and coccidia that are threats to young and middle age of chickens and after.

Specifically, in diseases in which the genes of neutralizing antigens or the genes of antigens that are considered immunoprotective antigens have been identified, it is possible to integrate these genes into avian infectious herpesviruses such as HVT and MDV and then to express them as antigens in the body of chickens that are infected with the integrated virus. This also makes it possible to use them as effective vaccines.

Specifically, proteins that are expressed in the birds infected with a recombinant virus constructed by integrating a gene into an avian infectious herpesvirus such as HVT or MDV may be any one of the structural protein or the non-structural protein, and are not limited as long as their DNA sequence is known.

For NDV, for example, there can be mentioned HN protein, F protein, and NP protein, and for IBV there can be mentioned M protein, N protein, and spike protein. For IBDV, there can be mentioned the entire protein comprising from VP1 to VP5, for ILTV, since it is a herpesvirus, proteins that are homologous to HSV-1, MDV, or HVT (specifically, gB protein or UL32-homologue protein), for mycoplasma, adhesin protein, HMW-related protein, 40K protein 66K protein, 67K protein, and the like (sequences are described in International Patent Publication WO 94/23019).

Thus, it is preferred to integrate genes encoding these proteins. Such foreign genes are called heterologous antigen genes.

In order to express a heterologous antigen gene in HVT or MDV, it is necessary to integrate a promoter sequence into a region upstream of the heterologous antigen gene. The promoter used may be either a synthetic or natural promoter, and is not limited as long as it can effectively function as such in a transcription system owned by the cell infected with HVT or MDV.

As such a promoters, not only a promoter inherently owned by HVT or MDV but also a promoter or DNA derived from a virus other than HVT or MDV, a promoter derived from an eukaryotic or prokaryotic organism, or a synthetic promoter can be used in the present invention, as long as they satisfy the above requirements.

Specifically, there can be mentioned the thymidine kinase promoter of herpesvirus (Ross L. J., Gen. Virol. 74:371–377 (1993)), gB protein promoter (supra) of HVT or MDV, the IE promoter of human cytomegalovirus (HCMV) (Alting-Mess M. A., Nucleic Acids Res., 17:9494 (1989)), SV40 promoter (Gunning P., Proc. Natl. Acad. Sci., 84:4931–4835 (1987)), β actin promoter (supra, and Kost A. T., Nucleic Acids Res., 11:8287–8301 (1983)), β-globin promoter (Spitzner J. R., Nucleic Acids Res., 18:1–11 (1990)), the LTR promoter of Rous sarcoma virus (Fiek A. et al., Nucleic Acids Res., 20:1785 (1992)), and the like. In addition, promoters of the structural proteins or the essential genes of HVT or MDV can also be used.

These may be integrated into the above-mentioned untranslated region in a manner such that a foreign antigen gene can be expressed under a control of a specific promoter, so as to construct a plasmid. The plasmid thus constructed may undergo recombination with a specific region of the HVT or MDV genome, thus resulting in the creation of a recombinant virus.

Construction of Recombinant Virus

The insertion of a foreign gene such as described above into an untranslated region of the genome of an avian infectious herpesvirus may be carried out according to a standard method. By way of example, HVT will be explained.

A plasmid in which a foreign antigen gene has been inserted into the HVT untranslated region obtained as above is introduced into an HVT-infected cell using electroporation, calcium phosphate, a lipofectin-based method, a gene gun method or the like. Because of the high efficiency of introduction, electroporation or a method employing lipofectin is preferred. When the amount of the plasmid to be introduced is in the range of 0.1 to 1000 $\mu$g, the efficiency of generation of recombinant viruses by recombination between the homologous regions of HVT-DNA and the plasmid becomes high in cells into which the kiasmid has been introduced.

In order to select only a recombinant HVT thus created, one or a plurality of foreign genes are integrated into the untranslated region of the plasmid, and at least one of the genes used is an enzyme gene for color generation from a specific substrate. Examples of such an enzyme gene include β-galactosidase gene.

A recombinant HVT containing the β-galactosidase gene can be clearly distinguished from non-recombinant viruses because it develops a specific color by the addition of a substrate such as Bluogal. Therefore, by culturing cells infected with a virus that has integrated such a gene, in a culture medium supplemented with a specific substrate, it is possible to select virus-infected cells that develops dolor. By repeating this procedure, recombinant viruses can be purified.

Live Vaccines

Methods of preparing a live vaccine of the present invention include, but are not limited to, the following methods.

Cells infected with a recombinant virus of the present invention is infected to the cells (hereinafter referred to as the host cell) in which said virus can propagate, and grown. Then cells are detached from the wells using a scraper or with trypsin and separate the infected cells are separated from the supernatant by centrifugation.

As host cells, cells derived from chicken are preferred, and CEF (chick embryo fibroblast), chicken kidney cells, and the like, can be preferably used.

The infected cells thus obtained are suspended in a culture medium containing 10% dimethyl sulfoxide (DMSO) and stored frozen under liquid nitrogen. When they are used as a vaccine, the frozen product is dissolved in 100 volumes of phosphate buffer prior to use.

Stabilizers and other components for use in storing said infected cells under liquid nitrogen are not limited as long as they enable the virus-infected cells to grow stably and they are pharmaceutically acceptable.

Methods of inoculating a live vaccine of the present invention to poultry include, but are not limited to, a conventionally used subcutaneous injection, and is the same as used in the current HVT vaccines. The amount to be inoculated may also the same as the conventional vaccines.

The vaccine of the present invention can be used not only as a vaccine for infections of herpesviruses but also as a vaccine for diseases caused by an antigen gene inserted into the untranslated region by the pathogen from which the genes are derived. The vaccine of the present invention can be used as a useful recombinant HVT multi-valent vaccine.

EXAMPLES

The present invention will now be explained in more detail with reference to the following Examples, but it must not be construed that the present invention is limited by these examples.

Example 1

Preparation of HVT-DNA

HVT-DNA was prepared essentially according to the method of Lee et al. (J. of Virol., 7:289–294 (1971)).

HVT(FC-126 strain)-infected cells ($5 \times 10^7$ cells) cultured in a Leibowitz-L-15/McCoy 5A (1:1) mixed medium in a 16 cm diameter culture dish at 37° C. for 4 days were scraped by a scraper and then centrifuged at a low speed (2,000 rpm, 5 minutes). After discarding the supernatant, a lysis buffer (0.15 M NaCl, 0.1 M EDTA, 1% SDS, 100 µg/ml proteinase K) in an amount 10 times that of the infected cells that precipitated was added.

After incubating overflight at 37° C., an equal amount of phenol was added to denature proteins, and this procedure wag repeated twice for extracting HVT-DNA. The DNA extracted was collected by ethanol precipitation.

Example 2

Construction of pNZ45/46Sfi

Based on the information on the gCh gene (Coussens et al., J. Virol., 62:2373–2379 (1988)) of the MDV serotype 1 and the flanking EcoRI-BamHI fragment (Japanese Unexamined Patent Publication (Kokai) No. 6-292583) of the BamHI-B fragment, synthetic DNAs (primers 1 to 4) were designed to introduce a SfiI site between the ORF.

The above article by Coussens et al. describes UL44 and 45, whereas Japanese Unexamined Patent Publication Asokai) No. 6-292583 describes UL46.

Using the primers as described bellow, PCR wan carried out and an amplified product was cloned into pUC18.

From the HVT-FC126-infected CEF, DNA was harvested by the method of Example 1, and 100 ng of the DNA was used as the template. Furthermore, using a primer set A consisting of primer 1 (CCCCGAATTC ATGGAAGAAA TTTCC; SEQ ID NO: 1) and primer 2 (CGCGCGCCTT ATTGOCCAAA ACACACCTCT AACGGTTACT; SEQ ID NO: 2) (50 pmol each) and a primer set B consisting of primer 3 (GCGCGGCCAA TAAGGCCAA ACACAG-TAAC CGTTAGAGGT; SEQ ID NO: 3) and primer 4 (CCCCAAGCTT TCAAGTGATA CTGCGTGA; SEQ ID NO: 4) (50 pmol each), FCR was carried out by a conventional method. The reaction was stopped at the 30th cycle and about 1 µg each of the amplified products was obtained.

Using a mixture of these two PFR products (mixed ratio 1:1, 100 ng of each was mixed) as the template, 30 cycles of PCR (one cycle comprising 45° C. for 1 minute, 60° C. for 2 minutes, and 73° C. for 3 minutes) were carried out using primer 1 and primer 4, and thereby a SfiI site was introduced in between the ORFs of UL45h and UL46h.

The amplified product thus obtained was cleaved with EcoRI and HindIII, and the fragment was inserted into the EcoRI-HindIII site of pUC18 using 4 units of T4 ligase (manufactured by Takara Shuzo) by incubating at 16° C. for 30 minutes to construct pNZ45/46Sfi.

Example 3

Construction of pNZ44/45sfi

As in Example 2, using DNA (10 ng) obtained from the HVT-FC126 strain-infected CEF as a template, and using a primer set C consisting of primer 1 and primer 5 (GCGCGGCCAA TAAGGCCAAC ATCGGGACGT ACATCAT; SEQ ID NO: 5) (50 pmol each) and a primer set D consisting of primer 6 (GCGCGGCCTT ATTGGCCTTA AATACCGCGT TTGGAGTAAA; SEQ ID NO: 6) and primer 4 (50 pmol each), PCR was carried out as in Example 2. Amplified products of about 10 µg each were obtained.

Using a mixture of these two PCR products (mixed ratio 1:1, 100 ng of each was mixed) as a template, PCR was carried out using primer 1 (50 pmol) and primer 4 (50 pmol) as in Example 2, and thereby an Stir site was introduced in between the ORFs of UL44h (gCh of HSV-1 or gCh (gA) of MDV1) and UL45h.

The product was cleaved with EcoRI and HindIII, and the fragment obtained was inserted into the EcoRI-HindIII site of pUC18 as in Example 2 to construct pNZ44/45Sfi.

Example 4

Construction of pG1MCSpolyASfi (1) Construction of donor plasmid pGTPs

A synthetic DNA (5'-AGCTGCCCCCCCCGGCAAGCTTGCA-3' (SEQ ID NO: 7)) was inserted into the HindIII-PstI site of pUC18, and this portion was then repaired to double strand using DNA polymerase. Then a synthetic DNA (5'-TCGACATTTTTATGTAC-3' (SEQ ID NO: 8)) was inserted into the SalI-KpnI site of the plasmid obtained, which was similarly repaired double strand with DNA polymerase. Furthermore, an annealed product of two synthetic DNAs (5'-AATTCGGCCGGGGGGGCAGCT-3' (SEQ ID NO: 9) and 5'-GCCCCCCCGGCCG-3' (SEQ ID NO: 10)) was introduced to the SacI-EcoRI site of the plasmid. Finally, an about 140 bp DNA fragment obtained by digesting the plasmid pNZ1729R (Yanagida et al., J. Virol., 66:1402–1408 (1992)) with HindIII and SacI was inserted to the HindIII-SacI site of this plasmid, to construct a plasmid pGTPs.

(2) Construction of pGIMCSpolyASfi puC18 was cleaved with DraI, and an XhoI linker (manufactured by Takara Shuzo) was inserted therein as in Example 2 to construct pUC18X in which an XhoI site had been introduced.

This pUC18X was cleaved with HindIII and PstI, to which synthetic DNA 1 (AGCTTGCCAATAAGGCTGCA; SEQ ID NO: 11) and synthetic DNA 2 (ATGGCCCGCC GGCTGACCGC; SEQ ID NO: 12) were annealed to create a fragment. This was inserted into the above XhoI site using T4 ligase (manufactured by Takara Shuzo) to construct pU18XG.

In order to introduce a poly A addition signal and a SfiI site into the KpnI-EcoRI site of pU18XG, a fragment prepared by annealing a synthetic DNA 3 (GCGGTCAGCC GGCGGGCCAT; SEQ ID NO: 13): and synthetic DNA 4 (GGTAAACTGC AGACTTGGCA GT; SEQ ID NO: 14) was inserted using T4 ligase to construct pUCpolyASfi.

Into the RpnI-BamHI site of this pUCpolyASfi, a 36 bp KpnI-BamHI fragment of pGTPs described in Example 4 (1) was inserted to construct pMCSpolyASfi.

Into the HindIII-PstI site of this pMCSpolyASfi, synthetic DNA 5 (ACTGCCAAGT CTGCAGTTTA CC; SEQ ID NO: 15) was inserted as in Example 2 to construct pGIMCSpolyASfi.

Example 5

Construction of pRSV and pCMV

An about 600 bp of NsiI-NheI fragment containing the RSV promoter excised from pBK-RSV (manufactured by STRATAGENE) by double digestion with NsiI and NheI was inserted as in Example 2 into the PstI-XbaI site of PGIMCSpolyASfi that was obtained in Example 4, to construct pRSV.

Similarly, a NsiI-NheI fragment containing the CMV promoter of pBK-CMV (manufactured by STRATAGENE) was excised, and was introduced as in Example 2 into the PstI-XbaI site of pGIMCSpolyASfi that was obtained in Example 4, to construct pCMV.

Example 6

Construction of pCMV-HN (BglI⁻)

(1) Deletion of BglI Sites from the CMV Promoter of pCMV

Since three BglI sites are present in the CMV promoter of pCMV, PCR was carried out as described below to introduce mutation so as to delete the BglI sites. Mutation was carried out in the following manner.

Using pCMV (100 ng) constructed in Example 5 as a template, PCR was carried out under the same conditions as in Example 2 using a primer set E consisting of primer 7 (SEQ ID NO: 12) and primer 8 (SEQ ID NO: 15) and a primer set F consisting of M13P7 primer (manufactured by Toyoboseki Co., Ltd.) and primer 9 (SEQ ID NO: 13). About 10 μg of each of the amplified products was obtained.

Amplified products (100 ng each) obtained using the above 2 primer sets were mixed at a mixed ratio of 1:1. With the mixture as a template, PCR was carried out as in Example 2 using M13P7 primer and primer 8 to obtain about 10 μg of PCA product (1).

Similarly, with pCMV (100 ng) as a template, PCR was carried out as in Example 2 using a primer set E consisting of primer 10 (SEQ ID NO: 14) and primer 11 (GGCATAATGC ATGGCGGGCC AT; SEQ ID NO: 17), and primer 12 (ATGGCCCGCC ATGCATTATGCC; SEQ ID NO: 16) and M13P7 primer (manufactured by Toyoboseki Co., Ltd.).

Similarly with the 1:1 mixture of 100 ng each of the products of these two primer sets as a template, PCR was carried out, this time, using primer 10 and M13P8 primer to obtain an about 10 μg of PCR product (2).

Furthermore, the PCR product (1) and the PCR product (2) were mixed. Then using M13P7 primer and M13P8 primer, PCR was carried out as in Example 2 to obtain a CMV promoter in which the BglI sites were deleted.

(2) Construction of pUCCMV

Also, an about 600 bp of NsiI-NheI fragment containing the CMV promoter of pBK-CMV (STRATAGENE) was inserted into the PstI-XbaI site of pUC19 as in Example 2 to construct pUCCMV.

(3) Construction of pNZ87

(3-1) Construction of a Plasmid (pNZ76) in which the β-galactosidase Gene hag been ligated to 7.5K Promoter After digesting 10 μg of pMA001 (Shirakawa et al., Gene. 28:127- (1984)) with BamHI, it was extracted with phenol:chloroform (1:1), followed by ethanol precipitation to collect the β-galactosidase gene (about 3.3 kb).

On the other hand, after digesting 0.3 μg of pUC19 with BamHI, it was extracted with phenol:chloroform, followed by ethanol precipitation. The product was ligated to the β-galactosidase gene prepared as above to create a hybrid plasmid pNZ66.

Forty μg of pUWP-1 (a plasmid containing the promoter of DNA encoding a 7.5K dalton peptide of a vaccinia virus WR strain) was digested with HpaII and EcoRI, subjected to 1.5% low-melting point agarose gel electrophoresis (70 V, 6 hours) to separate an about 0.26 kb fragment containing 7.5K promoter, which was then extracted with phenol:chloroform (1:1), and then precipitated with ethanol to collect DNA. The adhesive end of the DNA fragment was blunt-ended using DNA polymerase.

After digesting 0.3 μg of pNZ66 with HincII, it was extracted with phenol:chloroform, followed by ethanol precipitation to collect a fragment, to which was ligated about 0.26 kb of the 7.5K promoter gene mentioned above, and the hybrid plasmid obtained was designated as pNZ76.

(3-2) Construction of Hybrid Plasmid pNZ87 Wherein a Promoter from a Hybrid Phage mp10-HN180 and the DNA of the HN Gene of NDV has been Ligated Under the Control the Promoter pNZ76 was digested with BamHI, which was then subjected to 0.8% agarose gel to collect an about 2.9 kb fragment containing no β-galactosidase gene.

On the other hand, after digesting the hybrid phage mp10-HN180 with BglII and BamHI, an about 1.8 kb DNA fragment of the NH gene was collected from a 0.8% agarose gel.

Both fragments were ligated by ligase. The plasmid obtained was used to transform a competent *E. coli* TG-1 strain, and a plasmid was extracted using a conventional method. A hybrid plasmid containing the HN gene was detected, which was designated as pNZ87.

(4) Construction of pNZ87CMV

Then, an about 1.8 kb BamHI-SacI fragment containing the HN gene of NOV was excised from pNZ87 constructed in (3). The fragment was inserted as in Example 2 into the BamHI-SacI site of pUCCMV to construct pNZ87CMV.

Since pNZ87CMV has BglI sites in the promoter region, the HindIII-BamHI fragment containing the CMV promoter region was replaced with a HindIII-BamHI fragment of the PCR-constructed CMV promoter without the BglI sites described in (1) to construct pCMV-HN (BglI⁻).

Example 7

Construction of RSV-F (1) Construction of pUCRSV-pA

An about 600 bp of NsiI-NheI fragment containing the RSV promoter of pBK-RSV (STRATAGENE) was inserted into the PstI-XbaI site of pUC19 as in Example 2 to construct pUCRSV.

Separately, with pBK-RSV (STRATAGENE, 100 ng) as a template, PCR was carried out as in Example 2 using primer 13 (CGGGAGCTCT AATTGTTTGT G; SEQ ID NO: 18) and primer 14 (CGGGAATTCG CTTACAATTT; SEQ ID NO: 19) (50 pmol each) to obtain a fragment having the pA additional signal of SV40 promoter contained in pBK-RSV.

The PCR-amplified fragment was double digested with SacI and EcoRI, and inserted as in Example 2 into the SacI-EcoRI site of pUCRSV to construct pUCRSV-pA.

(2) Construction of pNZ98.

A plasmid XLIII-10H (Virus Research, 7:214–255 (1987)) containing the F gene and HN gene of NDV was used.

Four µg of the plasmid XLIII-10H was digested with XbaI and, after the resulting adhesive end was blunt-ended with DNA polymerase, it was then extracted with phenol:chloroform (1:1), and collected by ethanol precipitation. The collected DNA was digested with BamHI, subjected to a 0.8% agarose gel elaetrophoresis to collect a fragment containing an about 2.1 kb of complete F gene.

On the other hand, the pNZ76 created as above was double digested with BamHI and SmaI to collect an about 3.0 kb BamHI-SmaI fragment lacking the lacZ gene portion. The collected fragment and a fragment containing an about 2.1 kb of complete F gene were ligated by ligase to transform a competent E. coli TG1 strain.

A plasmid was prepared by a procedure similar to the described above from a colony grown on an LB agar plate containing 50 µg/ml ampicillin. The plasmid was cleaved with restriction enzymes (BamHI and SmaI), the desired clone was confirmed and designated as pNZ98'. This pNZ98' contains the full-length F gene and an about 300 bp 5'-end of the HN gene. In order to remove this portion, pNZ98', was double digested with SmaI and KpnI, and an about 4,150 bp SmaI-KpnI fragment was collected by a 0.8% agarose gel electrophoresis. pNZ98' was also double digested with SmaI and AvaII, and an about 650 bp SmaI-AvaII fragment was collected by a 1.5% agarose gel electrophoresis.

These two fragments were mixed, and the resulting adhesive end was blunt-ended with DNA polymerase. The product was then used to transform E. Coli TG1 to obtain a transformant. The transformant was grown on an LB agar medium containing 50 µg/ml ampicillin. From the resulting colony, a plasmid was obtained as mentioned above. The plasmid was digested again with SmaI, and the cleaved products were selected to obtain pNZ98.

(3) From pNZ98 constructed in above (2), an about 1.8 kb BamHI-SacI fragment containing the F gene of NDV was excised, which was then inserted into the BamHI-SacI site of pUCRSV-pA as described in Example 2 to construct pNZ98RSV3.

pNZ98 was also cleaved with PstI and partially digested with BamHI to obtain a 125 bp fragment.

The collected fragment was substituted for a 75 bp PstI-BamHI fragment contained in pNZ98RSV3' to construct pNZ98RSVpA.

A 2,892 bp MluI-SacI-cleaved fragment of pRSV constructed in Example 5 and a 2,262 bp MluI-SacI-cleaved fragment of the F gene of NDV of pNZ98RSvpA were ligated to construct pRSV-F.

Example 8

Construction of pCMV-VP2S (Okayama)

(1) Construction of pCMV/MCS.

Into the BamHI-KpnI site of pCMV-HN (BglI⁻) constructed in Example 6, a 62 bp BamHI-KpnI fragment of pBluescript SK+ was inserted to construct pCMV/MCS.

(2) Construction of pCMV/MCSpA

Separately, with pBK-RSV (STRATAGENE) as a template, PCR was carried out as in Example 2 using primer 15 (CCGGGGCCCT AATTGTTTGT G; SEQ ID NO: 20) and primer 16 (CGGGGTACCG CTTACAATTT; SEQ ID NO: 21) to obtain a fragment having the pA additional signal of SV40.

The PCR-amplified fragment was double digested with ApaI and KpnI, and was inserted as in Example 2 into the ApaI-KpnI site of pCMV/MCS to construct pCMV/MCSpA.

(3) Construction of pCMV-VP2S

Furthermore, RNA was extracted, according to a conventional method, from an IBDV field isolate Okayama strain. The RNA was used to generate cDNA using reverse transcriptase and the cDNA synthesis kit (manufactured by Takara Shuzo).

With this cDNA as a template, primer 17 (GCAAGCTTGC GATGACGAAC CTGCF; SEQ ID NO: 22) and primer 18 (GCGTCGACTC ACCTCCTTAG GGCCC; SEQ ID NO: 23) were designed based on a region corresponding to VP2 of the sequence of the gene as set forth in Japanese Unexamined Patent Publication (Kokai) No. 62-503006.

Using these two primers, PCR was carried out as in Example 2 to obtain a region corresponding to the VP2 of IBDV.

Separately, pCMV/MCSpA was partially digested with HindIII, and then partially with SalI, to obtain a 3,687 bp fragment. The fragment of IBDV obtained by the above PCR was double digested with HindIII and SalI, which was then inserted into a 3,687 bp fragment as in Example 2 to construct pCMV-VP2S (Okayama).

Example 9

Construction of pUC18Xlac

The BamHI-SacI fragment of lacZ (Yanagida et al., J. Virol., 66:1402–1408 (1992)) was inserted as in Example 2 into the BamHI-SmaI site of pU18XG constructed in Example 4 to construct pUC18Xlac.

Example 10

Construction of pNZ45/46RSVlac and pNZ44/45RSVlac (1) Construction of pNZ45/46RSVlac Into the SfiI site of pNZ45/46Sfi constructed in Example 2, the BglI fragment of pRSV containing the RSV promoter constructed in Example 5 was inserted to construct pNZ45/46RSV.

Into the Sfi site of pNZ45/46RSV, the BglI fragment of pUC18Xlac containing lacZ constructed in Example 9 was inserted to construct pNZ45/46RSVlac (2) Construction of pNZ44/45RSVlac Similarly, into the SfiI site of pNZ44/45Sfi constructed in Example 3, the BglI fragment of pRSV containing the RSV promoter constructed in Example 5 was inserted to construct pNZ45/46RSV.

Into the SfiI site of pNZ44/45RSV, the BglI fragment of pUC18Xlac containing lacz constructed in Example 9 was inserted to construct pNZ44/45RSVlac.

Example 11

Construction of pNZ45/46VP2S and pNZ44/45VP2S (1) Construction of pNZ45/46VP2S

Into the SfiI site of pNZ45/46RSVlac constructed in Example 10, the BglI fragment of pCMV-VP2S (Okayama) containing the VP2 gene of IBDV constructed in Example 8 was inserted as in Example 2 to construct pNZ45/46VP2S.

(2) Construction of pNZ44/45VP2S

Similarly, into the SfiI site of pNZ44/45RSVlac constructed in Example 10, the BglI fragment of pCMV-VP2S (Okayama) containing the VP2 gene of IBDV constructed in Example 8 was inserted as in Example 2 to construct pNZ44/45VP2S.

Example 12

Construction of pNZ45/46HNF and pNZ44/45HNF (1) Construction of pNZ45/46HNF

Into the SfiI site of pNZ45/46RSVlac constructed in Example 10, the BglI fragment of pCMV-HN (BglI⁻) containing the HN gene of NDV constructed in Example 6 was inserted as in Example 2 to construct pNZ45/46HN. Furthermore, into the SfiI site of pNZ45/46HN, the BglI fragment of pRSV-F containing the F gene of NDV constructed in Example 7 was inserted to construct pNZ45/46HNF.

(2) Construction of pNZ44/45HNF

Similarly, into the SfiI site of pNZ45/45RSVlac constructed in Example 10, the BglI fragment of pCMV-SN (BglI⁻) containing the HN gene of NDV constructed in Example 6 was inserted to construct pNZ44/45HN. Furthermore, into the SfiI site of pNZ44/45HN, the BglI fragment of pRSV-F containing the F gene of NDV constructed in Example 7 was inserted to construct pNZ44/45HNF.

Example 13

Construction of pNZ45/46HNF-VP25 and pNZ44/45VP2S-HNF (1) Construction of pNZ45/46HNF-VP2S Into the SfiI site of pNZ45/46HNF constructed in Example 12, the BglI fragment of pCMV-VP2S (Okayama) containing the VP2 gene of IBDV constructed in Example 8 was inserted to construct pNZ45/46HNF-VP2S.

(2) Construction of pNZ44/45VP2S-HNF

Into the SfiI site of pNZ44/45VP2S constructed in Example 11, the BglI fragment of pCMV-HN (BglI⁻) containing the RN gene of NDV constructed in Example 6 was inserted to construct pNZ44/45VP2S-HN. Furthermore, into the SfiI site of pNZ44/45VP2S-HN, the BglI fragment of pRSV-F containing the F gene of NDV constructed in Example 7 was inserted to construct pNZ44/45VP2S-HNF.

Example 14

Purification of Recombinant HVT

A monolayer of CEF that was detached with trypsin was suspended in Saline G (0.14 M sodium chloride, 0.5 mM potassium chloride, 1.1 mM hydrogen disodium phosphate, 1.5 mM dihydrogen sodium phosphate, and 0.5 mM magnesium chloride hexahydrate, 0.011% glucose) to prepare a cell suspension. The cell suspension ($2 \times 10^7$ cells) was mixed with 40 μg each of recombinant plasmid pNZ44/45VP2S, pNZ44/45HNF, pNZ45/46VP2S, pNZ45/46HNF, pNZ44/45VP2S-HNF, and pNZ45/46HNF-VP2S, and 100 μg each of the DNA of HVT prepared in Example 1.

After allowing the solution to stand at room temperature for 10 minutes, it was electroporated using the Gene Pulser (manufactured by Bio-Rad) at room temperature under the condition of 3.0 KVcm$^{-1}$, 0.4 msec, and 25° C.

The cells into which the plasmid and the DNA of HVT were introduced were plated on a culture dish of 9 cm in diameter (manufactured by Falcon), and then were cultured at 37° C. for about 4 to 5 days until plaques peculiar to HVT were formed.

Cells that formed plaques-were scraped with 1% trypsin, and were mixed with CEF cells ($2 \times 10^7$ cells) that were similarly scraped with trypsin, which was limiting-diluted in 10 96-well flat-bottomed multi culture plates (manufactured by Falcon). These plates were further cultured at 37° C. for about 4 to 5 days until plaques peculiar to HVT were formed in each well. Then, to a half of the wells in each plate, 100 μl/well of the CEF culture medium containing 100 μg/ml of Bluogal (manufactured by Gibco) which is a chromogenic substrate for β-galactosidase and 0.8% agar was added, and the plates were incubated at 37° C. for about 4 hours.

Thereafter, the number of blue plaques in each well was counted. A plate having the largest number of blue plaques was selected, to which 1% trypsin was added to collect CEF containing recombinant HVT-infected cells. The CEF was mixed with $1 \times 10^6$ cells, which was then plated on a 96-well flat-bottomed multi culture plate.

Screening Steps (one screening Step comprises one step of passaging from a 96-well flat-bottomed multi culture plate to a 96-well flat-bottomed multi culture plate) were repeated until all wells showed blue plaques, and were repeated until all plaques turned blue when Bluogel was added, and thereby the virus was purified. Purification is normally accomplished by screening about 5 to 10 times.

After the infected cells were grown on a culture dish of 9 cm in diameter, the infected cells were further grown on a culture dish of 16 cm in diameter. When the titer of the recombinant HVT was determined, the titer of the recombinant HVT was found to be 1 to $6 \times 10^3$ TCID$_{50}$.

The recombinant HVT prepared from each recombinant plasmid was designated as in the following table:

TABLE 1

| Name of recombinant plasmid | Name of recombinant HVT |
| --- | --- |
| pNZ44/45VP2S | HF002 |
| pNZ45/46VP2S | HF003 |
| pNZ44/45HNF | HF004 |
| pNZ45/46HNF | HF005 |
| pNZ44/45HNF-VP2S | HF006 |
| pNZ45/46HNF-VP2S | HF007 |

Example 15

Southern Hybridization

Recombinant virus DNA (HF003, HF004) prepared in Example 14 was extracted by the same method of extracting HVT-DNA as in Example 1.

The recombinant virus DNA (HF003, HF004) obtained, plasmids (pNZ/45/46VP2S, pNZ44/45HNF) for their recombination, and the DNA of the parent virus strain were digested with BamHI, which were then subjected to a 0.8% agarose gel electrophoresis and were analyzed by Southern blot hybridization and autoradiography.

The probe used is a $^{32}$P-labeled probe DNA prepared by digesting pNZ45/46VP2S or pNZ44/45HNF with EcoRI to obtain a fragment and then labeling the fragment using the Multi-Prime Labeling System (manufactured by Amersham).

The result revealed that sequences homologous to the probe DNA are present in recombinant HVTs.

Example 16

Confirmation of Expression of Foreign Antigen in Recombinant HVT-infected Calls (Fluorescent Antibody Method)

On a chamber slide for tissue culture, the above recombinant HVT-infected cells are cultured together with CEF at 37° C. until plaques developed, which were then fixed in cold acetone.

In order to detect the expressed antigen, the following were used as primary antibodies. For the detection of β-galactosidase, anti-β-galactosidase rabbit antiserum (polyclonal antibody: manufactured by Organon Teknica H. V.), and for the detection of NDV-NH protein and F protein, NDV vaccine-immunized chicken serum were used each at 500-fold dilution in PBS. For the detection of IBDV-VP2 protein, anti-VP-2 monoclonal antibody GK-5 (Yamaguchi T., et al., Avian Dis., 40:501–509 (1996)) was used at a 100-fold dilution in PBS.

As labeled antibody, FITC-labeled anti-chicken IgG antibody, FITC-labeled anti-mouse IgG antibody, and FITC-labeled anti-rabbit IgG antibody (all manufactured by Harlan Sera-Lab Ltd.) were each diluted 100-fold in PBS prior to use.

Each solution containing the above antibody was contacted with cells fixed in cold acetone on the chamber slide, allowed to stand at room temperature at a 100% humidity for about 1 hour, and then washed three times in PBS. Then, each solution was allowed to react at room temperature for about 1 hour together with dilutions of FITC-labeled anti-chicken immunoglobulin antibody or anti-mouse IgG. Then each solution was washed three times in PBS, and the reactivity was investigated by examining it under microscope at a fluorescence excitation wavelength (493.5 nm).

As a control virus, an HVT parent strain FC-126 was infected, and the cells infected with this parent strain were used as the control cells. The result is shown in Table 2.

TABLE 2

Reactivity to the primary antibody

| Infected virus | Anti-HN Mab | Anti-F Mab | Anti-VP2 Mab | Anti-β-gal |
|---|---|---|---|---|
| HF002 | − | − | + | + |
| HF003 | − | − | + | + |
| HF004 | + | + | − | + |
| HF005 | + | + | − | + |
| HF006 | + | + | + | + |
| HF007 | + | + | + | + |
| FC126 | − | − | − | − |
| Uninfected cell | − | − | − | − |

In the table, Mab represents monoclonal antibody.
+: reacted; −: not reacted.

The recombinant HVT that has incorporated the NDV antigen gene reacted with anti-NDV monoclonal antibody, whereas the recombinant HVT that has incorporated IBDV-VP2 gene reacted with anti-VP2 monoclonal antibody.

The result confirmed that each recombinant HVT was expressing protein encoded by the inserted gene.

Example 17

Experiment on the Effect of Chick Vaccine on NDV (SPF Chicks)

An experiment on the vaccination effect was carried out in order to determine the effects of the recombinant HVT vaccine obtained in Example 14.

Ten test SPF chicks (Line M. Nippon Institute for Biological Science) per group were inoculated with a recombinant HVT shown in Table 2. A commercial live vaccine was inoculated to the positive control group, and the negative control had no vaccination.

When test SPF chicks were hatched, each recombinant HVT was subcutaneously inoculated on the back of the chick using a 26 G needle to give $10^4$ $TDID_{50}$. The commercial live vaccine (Nippon Institute for Biological Science) used for the positive control was inoculated to 4-day old chicks by eyedropping according to the instructions.

At 4 weeks after inoculation, chicks of each group were challenged with virulent NDV (Sato strain) at $10^4$ PFU into the right thigh. The survival of chicks and the onset of NDV in chicks about 2 weeks after the challenge were observed to determine the effects using the survival rate as an index.

Before challenging the chicks with the ND virus, blood was drawn from each chick and the serum therefrom was tested to detect antibodies that suppress hemagglutination activity of NDV. The determination was carried out according to the instructions in the commercially available NDV hamagglutinin (Nippon Institute for Biological Science). The result is shown in Table 3.

TABLE 3

The result of the NDV challenge test for recombinant HVT (No. 1)

| Inoculated virus | Chicks survived/ chicks tested | Survival rate (%) |
|---|---|---|
| HF004 | 10/10 | 100 |
| HF005 | 10/10 | 100 |
| HF006 | 10/10 | 100 |
| HF007 | 10/10 | 100 |
| FC126 | 0/10 | 0 |
| NDV commercial vaccine | 10/10 | 100 |
| Not inoculated | 0/10 | 0 |

In chicks that received recombinant HVT, 100% protection against infection was accomplished for the challenge by NDV. The HI antibody titer was as low as 2-fold or lower in the FC126-inoculated chick group and the non-inoculated chick group, whereas it was 128-fold to 1024-fold in all chicks in the other groups.

The above result revealed that each recombinant HVT conferred to the inoculated chicks protection against infection by NDV.

Example 18

Experiment on the Affect of the Chick Vaccine on IBDV (SPF Chicks)

An experiment on the vaccination effect was carried out in order to determine the effects of the recombinant HVT vaccine obtained in Example 14.

Ten test SPF chicks (Line M. Nippon Institute for Biological Science) per group were inoculated with HF003 and FPV. A commercial vaccine was inoculated to the positive control group, and the negative control received no vaccines.

When test SPF chicks were hatched, each recombinant HVT was subcutaneously inoculated on the back of the chick using a 26 G needle to give $10^4$ $TCID_{50}$. The commercial NDV live vaccine (Kitasato Kenkyuusho) as the positive control was inoculated to 16-day old chicks by eyedropping according to the instructions.

At 17 days after inoculation, chicks of each group were challenged by oral administration of an attenuated IBDV virus (Okayama strain) at $1.5 \times 10^{3.8}$ $EID_{50}$. At about 3 days after challenging, chicks were examined whether they were alive or dead. Then the chicks that were alive were sacrificed and the onset of IBDV was examined using the state of lesion formation of the bursa of Fabricius as an index. The state of lesion formation of the bursa of Fabricius was judged based on scoring of 4 parameters; hemorrhage (A), yellowish exudate (B), discoloration (C), and gelatinous exudate (D). The score of each lesion was represented by the number of chicks that formed lesions, and the total score was used to determine the effect of the vaccine inoculated. The result is shown in Table 4.

TABLE 4

The result of IBDV challenge for recombinant HVT

| Inoculated virus | Chicks survived | Chicks that developed disease | A | B | C | D | Lesion score |
|---|---|---|---|---|---|---|---|
| HF003 | 10/10 | 6/10 | 2/6 | 1/6 | 3/6 | 0/6 | 6 |
| FPV | 9/10 | 9/10 | 7/9 | 6/9 | 8/9 | 6/6 | 27 |
| commercial vaccine | 10/10 | 3/10 | 1/3 | 0/3 | 2/3 | 0/3 | 3 |
| Not inoculated | 10/10 | 3/10 | 7/10 | 9/10 | 8/10 | 5/10 | 29 |

Chicks that received the recombinant HVT exhibited an ability of protecting against infection to a degree almost equal to that of the commercial vaccine for IBDV challenge.

The result revealed that the inoculation of recombinant HVT conferred protection against infection by IBDV.

Example 19

Experiment on the Effect of Chick Vaccine (Chicks having Maternal Antibody)

The recombinant HVT obtained in Example 14 was inoculated to commercial chicks to investigate the presence of vaccination effect on chicks having maternal antibody.

Chicks used are primary chicks born to commercially available white Leghorn (Dekalb chick, Kanagawa Youkei Rengokai (Kanagawa Poultry Farmers Association)). HF004 and HF006 were subcutaneously inoculated as in Example 17 on the back of the chick.

From 20 chicks of the same lot, blood was drawn by cardiocentesis and serum was obtained. After week 8 when maternal antibody had completely disappeared, challenge with NDV was carried out as in Example 17, and then the protection against infection was evaluated in terms of survival rate. The result is shown in Table 5.

TABLE 5

The result of the NDV challenge test for recombinant HVT (No. 2)

| Inoculated virus | Chicks survived/ chicks tested | Survival rate (%) | HI antibody titer |
|---|---|---|---|
| HF004 | 19/20 | 95 | 16 |
| HF006 | 18/20 | 90 | 15.5 |
| FC126 | 0/20 | 0 | <2 |
| NDV commercial vaccine | 14/19 | 74 | 8 |
| Not inoculated | 0/20 | 0 | <2 |

The antibody titer of the primary chicks was 97 (mean titer of 20 chicks).

The result revealed an almost perfect vaccination effect on NDV challenge for the group that received the recombinant HVT. The HI antibody titer at the time of challenge was also evidently higher than the FC126 inoculation group (<2) and the non-inoculation group (<2) (16 and 15.5).

In between HF004 and HF006 there were no significant differences, indicating that significant immunization effects can be conferred to the chicks regardless of the amount of antigen inserted.

As can be seen from these results, all the recombinant HVT described herein made an effective vaccine for diseases derived from the inserted antigen gene. In addition, it is free from the effects of maternal antibody.

Furthermore, the usefulness as a multi-valent recombinant HVT vaccine was demonstrated since it exhibited effects regardless of the amount of antigen inserted.

Industrial Applicability

In accordance with the present invention, there is provided a recombinant herpesvirus of turkeys, in which a foreign gene has been inserted into a genetic region that is the untranslated region in the genome of the herpesvirus of turkeys, and a vaccine comprising said recombinant herpesvirus of turkeys.

What is claimed is:

1. An avian infectious recombinant herpesvirus comprising a foreign gene inserted into an insertion site in an untranslated genetic region in the genome, wherein said insertion site is selected from the group consisting of sites (1) between UL44 and UL45, and (2) between UL45 and UL46.

2. The recombinant virus according to claim 1 which said virus is herpesvirus of turkeys or Marek's disease virus.

3. The recombinant virus according to claim 1 wherein said untranslated region is an untranslated region present in the open reading frame of the herpesvirus of turkeys or in the open reading frame of the Marek's disease virus, each corresponding to the open reading frame of human herpes simplex virus.

4. The recombinant virus according to any of claims 1 to 3 wherein said foreign gene is an antigen gene of a pathogen of avian infections selected from the group consisting of viral pathogen, bacterial pathogen, fungal pathogen, and protozoa pathogen.

5. The recombinant virus according to claim 4 wherein said pathogen of avian infections is a pathogen selected from the group consisting of virus, bacteria, fungi, and protozoa.

6. The recombinant virus according to claim 4 wherein said pathogen of avian infections is a pathogen selected from the group consisting of Newcastle disease virus (NDV), Gumboro disease virus (infectious bursal disease virus: IBDV), infectious laryngotracheitis virus (ILTV), infectious bronchitisvirus (IBV), mycoplasma (MG), and coccidia.

7. The recombinant virus according to any of claims 1 to 3 which has a promoter upstream of said foreign gene.

8. A chicken vaccine comprising a recombinant virus according to any of claims 1 to 3.

9. The recombinant herpesvirus according to claim 1, wherein the foreign gene is an antigen gene.

10. The recombinant virus according to claim 4 wherein the pathogen of avian infections is selected from the group consisting of Newcastle Disease Virus (NDV), Gumboro disease (infectious bursal disease virus) (IBDV), infectious laryngotracheitis virus (ILTV), infectious bronchitis virus (IBV), mycoplasma (MG), and coccidia.

11. An avian infectious recombinant herpesvirus comprising a foreign gene consisting essentially of a gene selected from VP2 of IBDV, HF of NDV and F of NDV inserted into a genetic region that is an untranslated region in the genome selected from UL44-UL45 and UL45-UL46 of HVT.

12. The recombinant virus according to claim 11 which has a promoter upstream of said foreign gene.

13. The recombinant virus according to claim 10, wherein the foreign gene is inserted at a SfiI site in the untranslated region.

14. The recombinant virus according to claim 13, wherein the foreign gene is inserted in the UL44-UL45 untranslated region using a first primer set of SEQ ID NO:1 and SEQ ID NO:5 and a second primer set of SEQ ID NO:6 and SEQ ID NO:4.

15. The recombinant virus according to claim 13, wherein the foreign gene is inserted in the UL45-U46 untranslated region using a third primer set of SEQ ID NO:1 and SEQ ID NO:2 and a fourth primer set of SEQ ID NO:3 and SEQ ID NO:4.

16. The recombinant virus according to claim 11, wherein the foreign gene is VP2 of IBDV inserted into the untranslated region UL44-UL45 of HVT.

17. The recombinant virus according to claim 11, wherein the foreign gene is VP2 of IBDV inserted into the untranslated region UL45-UL46 of HVT.

18. The recombinant virus according to claim 11, wherein the foreign gene is HN and F of NDV inserted into the untranslated region UL44-UL45 of HVT.

19. The recombinant virus according to claim 11, wherein the foreign gene is HN and F of NDV inserted into the untranslated region UL45-UL46 of HVT.

20. The recombinant virus according to claim 11, wherein the foreign gene is VP2 of IBDV and HN and F of NDV inserted into the untranslated region UL44-UL45 of HVT.

21. The recombinant virus according to claim 11, wherein the foreign gene is VP2 of IBDV and HN and F of NDV inserted into the untranslated region UL45-UL46 of HVT.

22. The recombinant virus according to claim 11, wherein the foreign gene consists of at least one gene selected from VP2 of IBDV, HF of NDV and F of NDV.

23. A chicken vaccine comprising a recombinant virus according to any of claims 11 to 22.

24. An avian infectious recombinant herpesvirus selected from HVT and MDV, said herpesvirus comprising a foreign gene inserted into an insertion site in an untranslated genetic region in the genome, wherein said insertion site is selected from the group consisting of sites (1) between UL44 and UL45, and (2) between UL45 and UL46.

25. The recombinant herpesvirus according to claim 24, wherein the foreign gene is selected from VP2 of IBDV, HN of NDV and F of NDV.

* * * * *